(12) United States Patent
La Berge

(10) Patent No.: US 10,226,570 B2
(45) Date of Patent: Mar. 12, 2019

(54) APPARATUS AND METHOD FOR TEMPORARILY SECURING A MOVABLE ACCESSORY DEVICE RELATIVE TO A MOVABLE PATIENT

(71) Applicant: SETON HEALTHCARE FAMILY, Austin, TX (US)

(72) Inventor: Christopher La Berge, Austin, TX (US)

(73) Assignee: SETON HEALTHCARE FAMILY, Austin, TX (US)

( * ) Notice: Subject to any disclaimer, the term of this patent is extended or adjusted under 35 U.S.C. 154(b) by 0 days.

(21) Appl. No.: 15/915,257

(22) Filed: Mar. 8, 2018

(65) Prior Publication Data

US 2018/0256814 A1 Sep. 13, 2018

Related U.S. Application Data

(60) Provisional application No. 62/469,937, filed on Mar. 10, 2017.

(51) Int. Cl.
*F16B 45/00* (2006.01)
*A61M 5/14* (2006.01)
(Continued)

(52) U.S. Cl.
CPC .......... *A61M 5/1415* (2013.01); *A47D 15/00* (2013.01); *A61B 8/4405* (2013.01); *A61G 5/10* (2013.01);
(Continued)

(58) Field of Classification Search
USPC ........................................................ 248/304
See application file for complete search history.

(56) References Cited

U.S. PATENT DOCUMENTS

D31,995 S * 12/1899 Alker .............................. D8/370
712,898 A * 11/1902 Barney .................. A47C 1/124
297/248
(Continued)

OTHER PUBLICATIONS

"Hill-Rom 1000 Medical Surgical Bed" Accessed from the internet on May 4, 2018, URL: https://www.hill-rom.com/usa/Products/Category/Hospital-Beds/Hill-Rom-1000-medical-surgical-bed.
(Continued)

*Primary Examiner* — Monica E Millner
(74) *Attorney, Agent, or Firm* — Armstrong Teasdale LLP

(57) ABSTRACT

This disclosure includes apparatuses and methods for temporarily securing a movable accessory structure relative to a movable patient-support structure. Some of the present apparatuses include an S-shaped body having a front, a back, a top, a bottom, a first side, a second side, and a longitudinal axis extending through the first and second sides, the body defining a first hook on the first side, and a second hook on the second side, the first hook opening toward the front of the body to define a first opening, and the second hook opening toward the back of the body to define a second opening. In some apparatuses, the first hook is dimensioned to receive a first member of the patient-support structure, and the second hook is dimensioned to receive a second member of the accessory structure, such that the body will resist separation of the accessory structure from the patient-support structure during movement of the patient-support structure.

22 Claims, 13 Drawing Sheets

(51) Int. Cl.
*A61B 8/00* (2006.01)
*A61M 16/00* (2006.01)
*A61G 5/10* (2006.01)
*A47D 15/00* (2006.01)
*A61G 11/00* (2006.01)
*A61G 7/05* (2006.01)

(52) U.S. Cl.
CPC ............... *A61G 7/05* (2013.01); *A61G 11/00* (2013.01); *A61M 16/0003* (2014.02); *F16B 45/00* (2013.01); *A61M 2209/082* (2013.01)

(56) References Cited

U.S. PATENT DOCUMENTS

| | | | | |
|---|---|---|---|---|
| 810,004 | A * | 1/1906 | Tabler | F16L 3/13 114/364 |
| 1,598,403 | A * | 8/1926 | Stockard | A47G 25/12 248/113 |
| 2,216,876 | A * | 10/1940 | Crum | A47C 21/00 119/322 |
| 2,696,963 | A * | 12/1954 | Shepherd | A61M 5/1415 24/339 |
| 3,521,332 | A * | 7/1970 | Kramer | F16B 2/22 248/229.26 |
| 3,854,689 | A * | 12/1974 | Engels | A22B 7/002 248/340 |
| 4,023,762 | A * | 5/1977 | Batts | A47G 25/005 211/113 |
| 4,068,817 | A * | 1/1978 | Berger | G09F 7/22 248/303 |
| 4,729,576 | A | 3/1988 | Roach | |
| 4,887,785 | A * | 12/1989 | Blaich | A01K 39/00 24/716 |
| 5,112,074 | A * | 5/1992 | Smith | B60D 1/50 156/187 |
| 5,118,127 | A * | 6/1992 | Partington | A61G 7/05 267/291 |
| 5,149,036 | A | 9/1992 | Sheehan | |
| 5,219,139 | A * | 6/1993 | Hertzler | A61G 5/10 248/276.1 |
| 5,356,061 | A * | 10/1994 | Yu | B60R 7/043 211/106 |
| 5,358,205 | A * | 10/1994 | Starkey | F16B 7/0493 248/220.21 |
| 5,421,548 | A * | 6/1995 | Bennett | A61G 5/10 248/129 |
| D362,386 | S * | 9/1995 | Blocker | 294/137 |
| 5,482,239 | A * | 1/1996 | Smith | A61G 5/10 248/229.13 |
| 5,588,166 | A * | 12/1996 | Burnett | A61G 7/05 248/214 |
| 5,704,577 | A * | 1/1998 | Gordon | A61H 3/04 135/66 |
| 5,894,972 | A * | 4/1999 | Brown | A45F 5/1026 224/267 |
| 5,918,892 | A * | 7/1999 | Aaron | B62B 7/04 280/209 |
| 5,957,155 | A * | 9/1999 | Lovejoy | B05B 15/00 137/356 |
| 6,079,678 | A * | 6/2000 | Schott | A61G 7/05 248/125.1 |
| 7,232,105 | B2 * | 6/2007 | Want | A61G 7/0503 128/DIG. 24 |
| 7,637,464 | B2 * | 12/2009 | Heimbrock | A61G 1/04 248/218.4 |
| 8,177,736 | B2 * | 5/2012 | Kopperschmidt | A61M 1/3653 24/335 |
| 8,225,971 | B2 * | 7/2012 | Stark | A45C 13/38 224/255 |
| D704,834 | S * | 5/2014 | Bacon | D24/128 |

OTHER PUBLICATIONS

Google Shopping Search "IV Stand Attachment", Accessed from the internet on May 4, 2018.

* cited by examiner

APPARATUS AND METHOD FOR TEMPORARILY SECURING A MOVABLE ACCESSORY DEVICE RELATIVE TO A MOVABLE PATIENT

CROSS-REFERENCE TO RELATED APPLICATIONS

This application claims the benefit of priority to U.S. Provisional Patent Application Ser. No. 62/469,937 filed Mar. 10, 2017, hereby incorporated by reference in its entirety.

FIELD OF INVENTION

The present invention relates generally to securing a movable accessory device relative to a movable patient support and more particularly, but not by way of limitation, to apparatuses and methods for temporarily securing a movable accessory device relative to a movable patient support to facilitate movement of the accessory device with the patient support.

BACKGROUND

Safely transporting a patient on intravenous (IV) fluids or medication, or connected to certain sensors, can be a challenging task for a health care provider (e.g., nurse, clinical assistant, respiratory therapist, or the like) when the patient is confined to, for example, a bed, crib, isolette, radiant warmer, wheel chair, or the like. When transporting a confined patient, the objective is to protect the patient and the IV line (or other accessory device lines connected to the patient), while ensuring the safety of the healthcare provider(s) moving the patient. However, ensuring both patient and provider safety during transport can be difficult when a patient is "hooked up" to an accessory device (e.g., an IV pole, sensor platform, ultrasound cart, crash cart, patient ventilator, or the like) that must be transported in tandem with the patient. For example, a healthcare provider may be required to push a bed or crib with one hand while towing an IV stand or other accessory device with the other hand. As another example, a wheelchair-bound patient moving himself or herself may be required to roll the wheelchair with one hand while holding their IV stand or other accessory device with the other hand. In either example, inadvertent disconnection of accessory device lines (e.g., an IV line, a feeding tube, a sensor line, and/or the like) may occur if the healthcare provider or patient loses control of the accessory device. One solution to this problem is to enlist a second person to tow the accessory device. Another solution is to secure the accessory device relative to the patient support. Examples of devices for securing an accessory device relative to a patient support are disclosed in: (1) U.S. Pat. No. 5,149,036; (2) U.S. Pat. No. 4,729,576; and (3) U.S. Pat. No. 5,219,139.

SUMMARY

This disclosure includes apparatuses and methods temporarily securing a movable accessory device relative to a movable patient support to facilitate movement of the accessory device with the patient support. The present apparatuses can be configured to facilitate tandem movement of an IV pole (or other accessory device) and a patient support (e.g., a bed, crib, isolette, radiant warmer, wheel chair, or the like). The present apparatuses, which include an "S-shaped" body defining dual opposing hooks, are relatively easy to use, clean, and store. In use, the present apparatuses allow a healthcare provider to use both hands to push and steer the patient support. The unique "S-shaped" body of the present apparatuses also allows them to be easily and conveniently hung for storage when not in use. The relative simplicity of the present apparatuses can also facilitate cleaning and disinfection.

Prior art devices may not be feasible to implement in a hospital setting due to cost, complexity of installation and use, and impracticality of disinfection (e.g., difficulties in disinfecting larger or more-complex shapes) and storage requirements (e.g., the requirement for impractically large or awkward spaces for storage of the devices). In contrast, the present apparatuses are relatively small, are simple to deploy, disinfect, and store, and need not be permanently secured to any single patient support or accessory device.

Some embodiments of the present apparatuses (e.g., for temporarily securing a movable accessory structure relative to a movable patient-support structure) comprise: an S-shaped body having a front, a back, a top, a bottom, a first side, a second side, and a longitudinal axis extending through the first and second sides, the body defining a first hook on the first side, and a second hook on the second side, the first hook opening toward the front of the body to define a first opening, and the second hook opening toward the back of the body to define a second opening; where the first hook is dimensioned to receive a first member of the patient-support structure, and the second hook is dimensioned to receive a second member of the accessory structure, such that the body will resist separation of the accessory structure from the patient-support structure during movement of the patient-support structure.

In some embodiments of the present apparatuses, the body is defined by an elongated member having a substantially constant cross-section along a majority of its length.

Some embodiments of the present apparatuses, further comprise an arm coupled to and extending downward from a portion of the body defining the first hook.

In some embodiments of the present apparatuses, the arm is defined by an elongated member having a substantially constant cross-section along a majority of its length. In some embodiments of the present apparatuses, the arm is not perpendicular to a plane of the first hook. In some embodiments, the arm has a length that is between 100% and 125% of a minimum width of the first opening. In some embodiments, the arm is integral with the body.

In some embodiments of the present apparatuses, an upper portion of the arm extends outward from the first side of the body and bends back inward toward the second side of the body. In some embodiments, a lower portion of the arm extends inward toward the second side of the body and bends back outward away from the second side of the body.

In some embodiments of the present apparatuses, the first hook terminates in a first end with a cross-section that is enlarged relative to that of a majority of the first hook. In some embodiments, the second hook terminates in a second end with a cross-section that is enlarged relative to that of a majority of the second hook. In some embodiments, the first hook includes a first sphere disposed at the first end, and the second hook includes a second sphere disposed at the second end, the first sphere having a diameter that is larger than a transverse dimension of a portion of the body that extends to the first sphere, and the second sphere having a diameter that is larger than a transverse dimension of a portion of the body that extends to the second sphere.

In some embodiments of the present apparatuses, the first opening has a first minimum width, the second opening has a second minimum width, and the body is configured to permit the first hook to flex to receive a first member having a first transverse dimension that is larger than the first minimum width, and to permit the second hook to flex to receive a second member having a second transverse dimension that is larger than the second minimum width.

In some embodiments of the present apparatuses, the first opening has a first minimum width, and the second opening has a second minimum width that is between 100% and 150% of the first minimum width. In some embodiments, the second minimum width is between 120% and 135% of the first minimum width. In some embodiments of the present apparatuses, the first minimum width is between 50 millimeters (mm) and 60 mm. In some embodiments of the present apparatuses, the first opening has a first maximum width that is larger than the first minimum width, and the first hook has a first maximum depth that is between 100% and 150% of the first minimum width. In some embodiments of the present apparatuses, the first maximum depth is between 120% and 135% of the first minimum width. In some embodiments, the second opening has a second maximum width that is larger than the second minimum width, and the second hook has a second maximum depth that is between 150% and 200% of the second minimum width. In some embodiments, the second maximum depth is between 175% and 185% of the second minimum width.

In some embodiments of the present apparatuses, the first hook lies in a first plane, and the second hook lies in a second plane that is angled along the longitudinal axis by 0 degrees to 30 degrees relative to the first plane. In some embodiments of the present apparatuses, the second plane is parallel to the first plane. In some embodiments of the present apparatuses, the second plane is coplanar with the first plane.

In some embodiments of the present apparatuses, the patient-support structure is a bed, a crib, an isolette, a radiant warmer, or a wheel chair.

Some embodiments of the present methods (e.g., for temporarily securing a movable accessory structure relative to a movable patient-support structure) comprise: disposing a first member of the patient-support structure within the first hook of an embodiment of the present apparatuses; disposing a second member of the accessory structure within the second hook of the apparatus; and moving the accessory structure by moving the patient-support structure. In some embodiments, the patient-support structure is a bed, a crib, an isolette, a radiant warmer, or a wheel chair. In some embodiments, the accessory structure comprises an IV pole, a sensor platform, an ultrasound cart, a crash cart, or a patient ventilator.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale for at least the embodiments shown.

DETAILED DESCRIPTION

Figure 1:
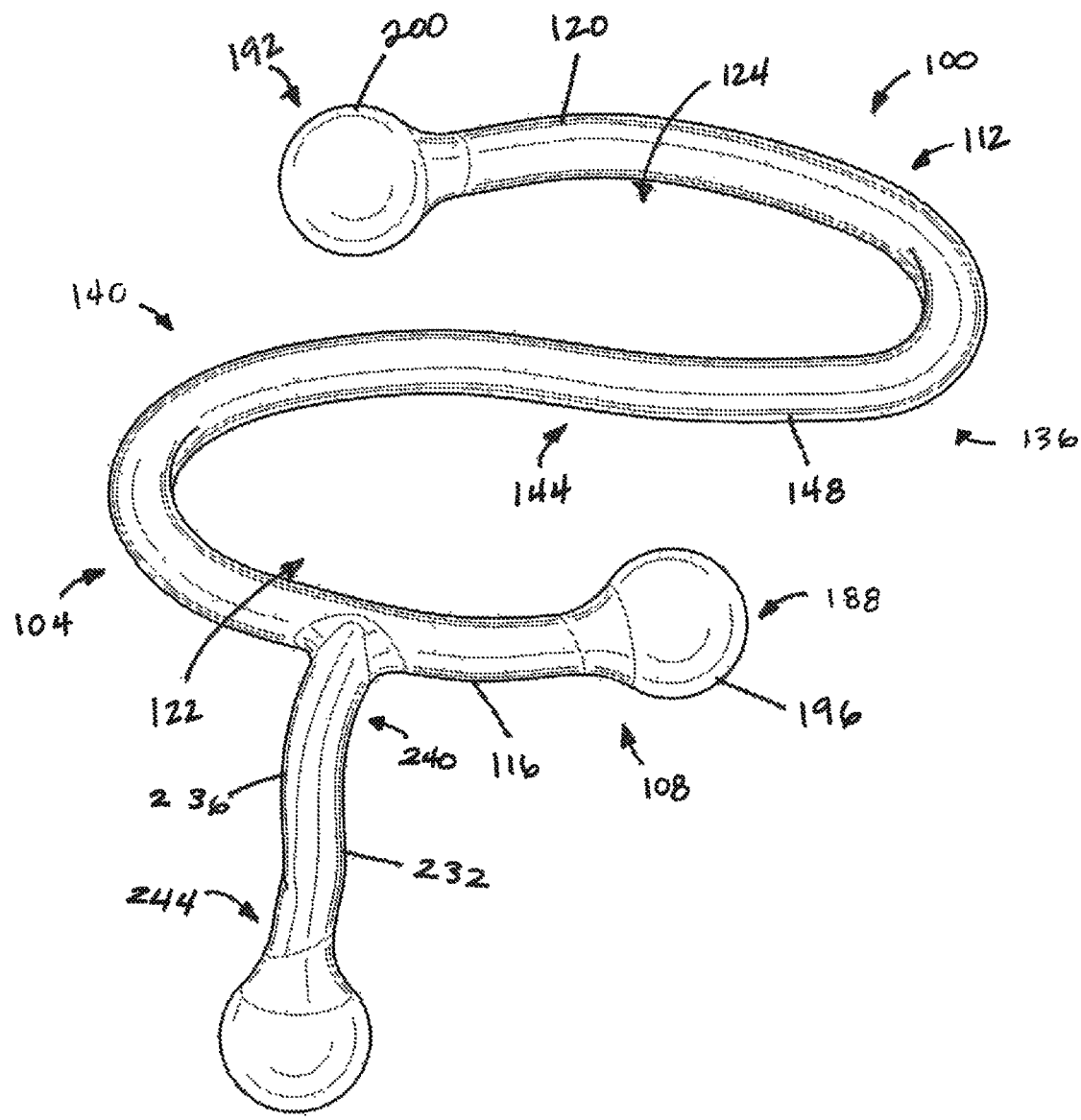
FIG. 1 depicts an upper perspective view of an embodiment of the present apparatuses.
Figure 2:
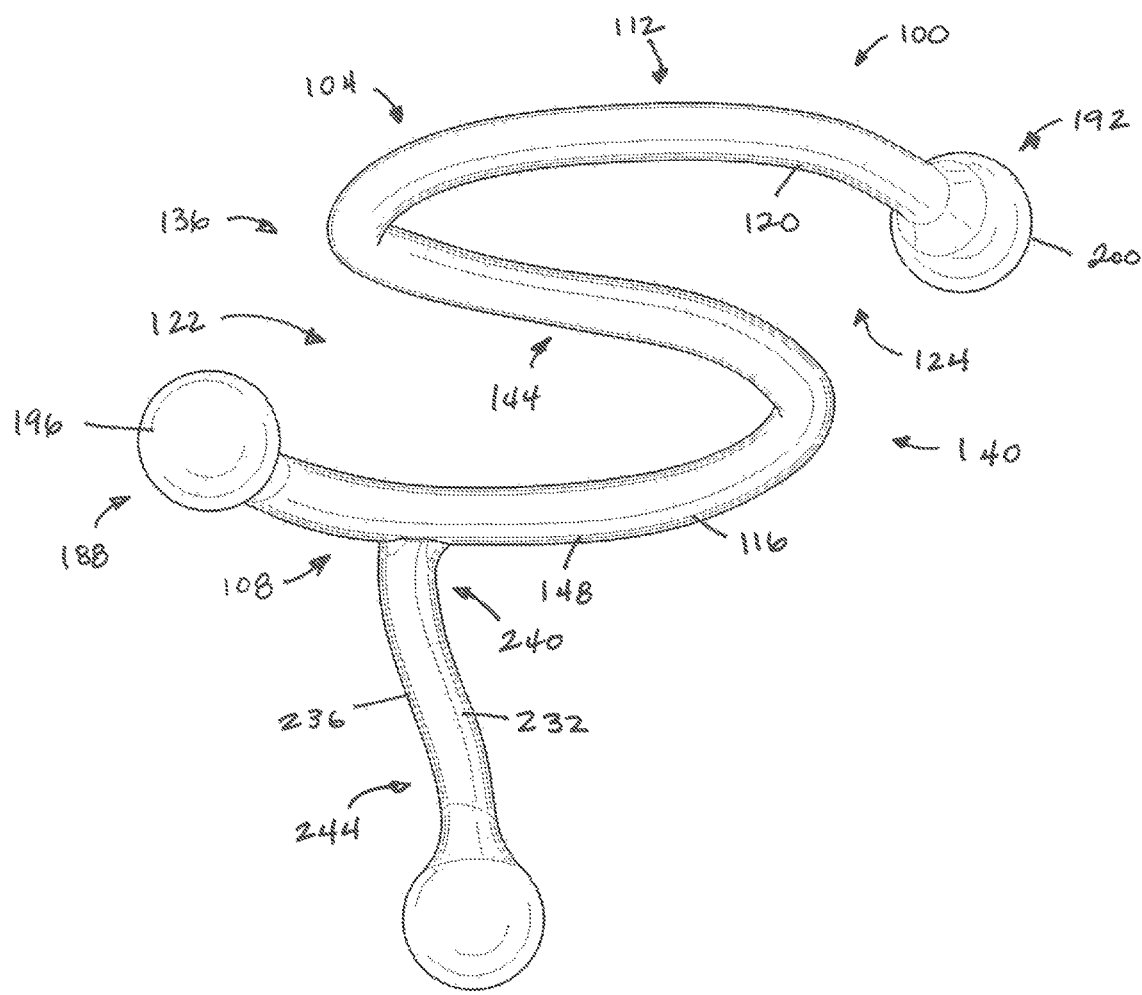
FIG. 2 depicts a lower perspective view of the apparatus of FIG. 1.

Referring now to the drawings, and more particularly to FIGS. 1-8, shown therein and designated by the reference numeral 100 is an embodiment of the present apparatuses. Apparatus 100 is for securing a movable accessory device (e.g., an IV pole, sensor platform, ultrasound cart, crash cart, patient ventilator, or the like) relative to a movable patient-transfer device (e.g., a bed, crib, isolette, radiant warmer, wheel chair, or the like). For example, apparatus 100 includes a body 104 having a first side 108 that defines a first hook 116, and a second side 112 that is opposite to the first side and defines a second hook 120. Hooks 116 and 120 each define an opening, first opening 122 and second opening 124, respectively, for receiving a member (e.g., a part) of a respective one of the accessory device and the patient-transfer device. In this way, the accessory device can be secured relative to the patient-transfer device such that, for example, movement of the patient-transfer device moves the accessory device.

In apparatus 100, body 104 is S-shaped. For example, hook 116 opens toward a front 136 of body 104, and hook 120 opens toward a back 140 of the body that is opposite to the front. Such an S-shaped cross-section can mitigate inadvertent separation of apparatus 100 from members of the accessory device and the patient-transfer device (e.g., by increasing an amount that each of hooks 116 and 120 surrounds its respective member), facilitate storage of the apparatus (e.g., the apparatus can be hung and removed from a rack by one of the hooks with less interference that might otherwise be caused by the other of the hooks), and/or the like.

Body 104 is defined by an elongated member 148 that extends between a first end 188 of hook 116 and a second end 192 of hook 120. In this embodiment, elongated member 148 has a circular cross-section that is substantially constant along a majority of its length (measured along the elongated member). In other embodiments, a body can be defined by an elongated member having any suitable cross-section, such as, for example, one that is triangular, rectangular, otherwise polygonal, circular, elliptical, or otherwise rounded, and the cross-section of the elongated member can be substantially constant or varying (e.g., in shape and/or dimensions) along any portion of its length.

Figure 3:
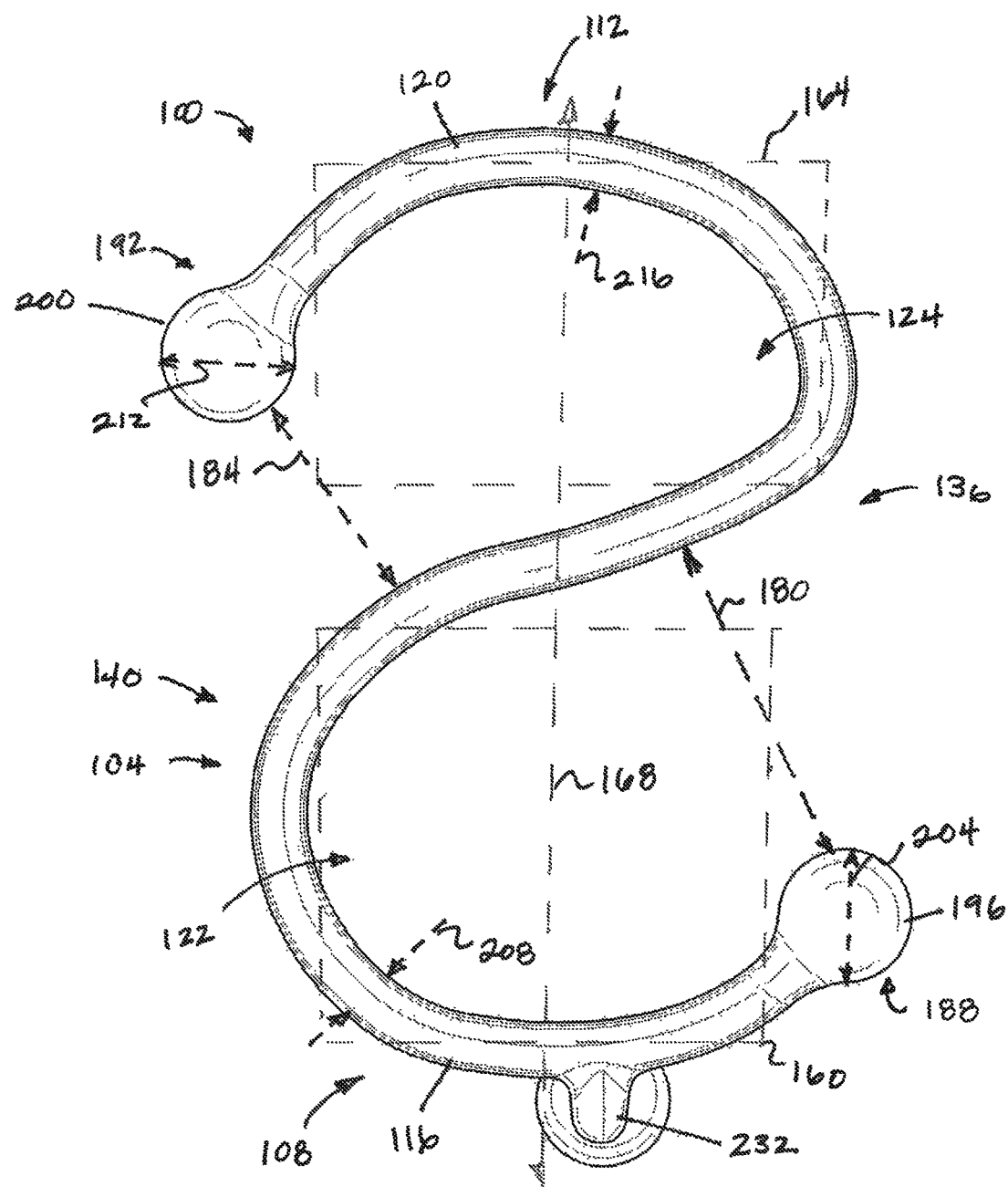
FIG. 3 depicts a top view of the apparatus of FIG. 1.

In apparatus 100, hooks 116 and 120 are co-planar; for example, hook 116 lies in a first plane 160, and hook 120 lies in a second plane 164 that is co-planar with the first plane (FIG. 3). A hook (e.g., 116) "lies in" a plane (e.g., 160) or the plane is "of the hook" if the plane intersects the hook along at least a majority of its length. In some embodiments, a plane of a first hook can be parallel to, but offset from, a plane of a second hook. In some embodiments, a plane of a first hook can be angularly disposed relative to a plane of a second hook. For example, an angle between the plane of the first hook and the plane of the second hook (e.g., about a longitudinal axis 168 of a respective body 104 that defines the hooks or an axis that is perpendicular thereto) can be greater than or substantially equal to any one of, or between any two of: 5, 10, 15, 20, 25, 30, 35, or 40 degrees.

Hooks (e.g., 116 and 120) of the present apparatuses (e.g., 100) can be defined by a body (e.g., 104) such that a portion of the body that defines a portion of one of the hooks also defines a portion of the other of the hooks or such that the hooks are contiguous. A body (e.g., 104) of the present apparatuses (e.g., 100) can include a medial portion disposed between its hooks (e.g., 116 and 120).

Hooks 116 and 120 can be configured to mitigate inadvertent separation of apparatus 100 from members of the accessory device and the patient-transfer device. For example, opening 122 of first hook 116 has a first minimum width 180, and body 104 is configured to permit the first hook to flex such that a member having a transverse dimension that is larger than the first minimum width can be disposed within the opening. Similarly, opening 124 of second hook 120 has a second minimum width 184, and body 104 is configured to permit the second hook to flex such that a member having a transverse dimension that is larger than the second minimum width can be disposed within the opening. A minimum width (e.g., 180) of an opening (e.g., 122) of a hook (e.g., 116) can be the minimum distance across the opening between the free end of the hook and a portion of its respective body (e.g., 104), measured when the body is in an unflexed state. In this way, each of hooks 116 and 120 can flex to receive a member within its opening, and, once the member is received by the opening, the hook can move toward its unflexed state to facilitate retention of the member within the opening. Such flexibility of body 104 can be provided by the body comprising a flexible material, such as, for example, a flexible metal (e.g., steel), a flexible plastic, and/or the like.

First minimum width 180 and second minimum width 184 can each comprise any suitable width, and such minimum widths can be, but need not be, the same. For example, first minimum width 180 can be greater than or substantially equal to any one of, or between any two of: 30, 35, 40, 45, 50, 55, 60, 65, or 70 millimeters (mm) (e.g., between 50 and 60 mm). For further example, second minimum width 184 can be greater than or substantially equal to any one of, or between any two of: 80, 90, 100, 110, 120, 130, 140, 150, 160, or 170% of first minimum width 180 (e.g., between 100 and 150% or between 120 and 135% of the first minimum width). Minimum widths 180 and 184 can be selected based on the dimensions of the members to which apparatus 100 is intended to be coupled.

Each of hooks 116 and 120 can have a cross-section at its end that is enlarged relative to other portions of the hook. For example, first hook 116 includes a first sphere 196 disposed at first end 188, the first sphere having a diameter 204 that is larger than a transverse dimension 208 of a portion of body 104 that extends to the first sphere. Similarly, second hook 120 includes a second sphere 200 disposed at second end 192, the second sphere having a diameter 212 that is larger than a transverse dimension 216 of a portion of body 104 that extends to the second sphere. Such enlarged portions can facilitate hooks 116 and 120 in receiving and/or retaining members within their respective openings and/or in removing members from within their respective openings. For example, for each of hooks 116 and 120, once a member is received within its opening, the enlarged portion can physically resist removal of the member from the opening. For further example, for each of hooks 116 and 120, the enlarged portion can control flexure of the hook as the member is received within and/or is removed from its opening (e.g., a profile of the enlarged portion can be selected to achieve a desired rate of flexure of the hook as the member moves along the enlarged portion; for example, a spherical enlarged portion can encourage the hook to "snap" around a member). Additionally, the physical transition between the elongated body of the hook and the enlarged portion (e.g., sphere) can be rounded or "filleted" as shown to reduce the likelihood of bacteria or other contaminants being trapped, thereby increasing the ease and efficacy with which the apparatus can be disinfected.

Figure 4:
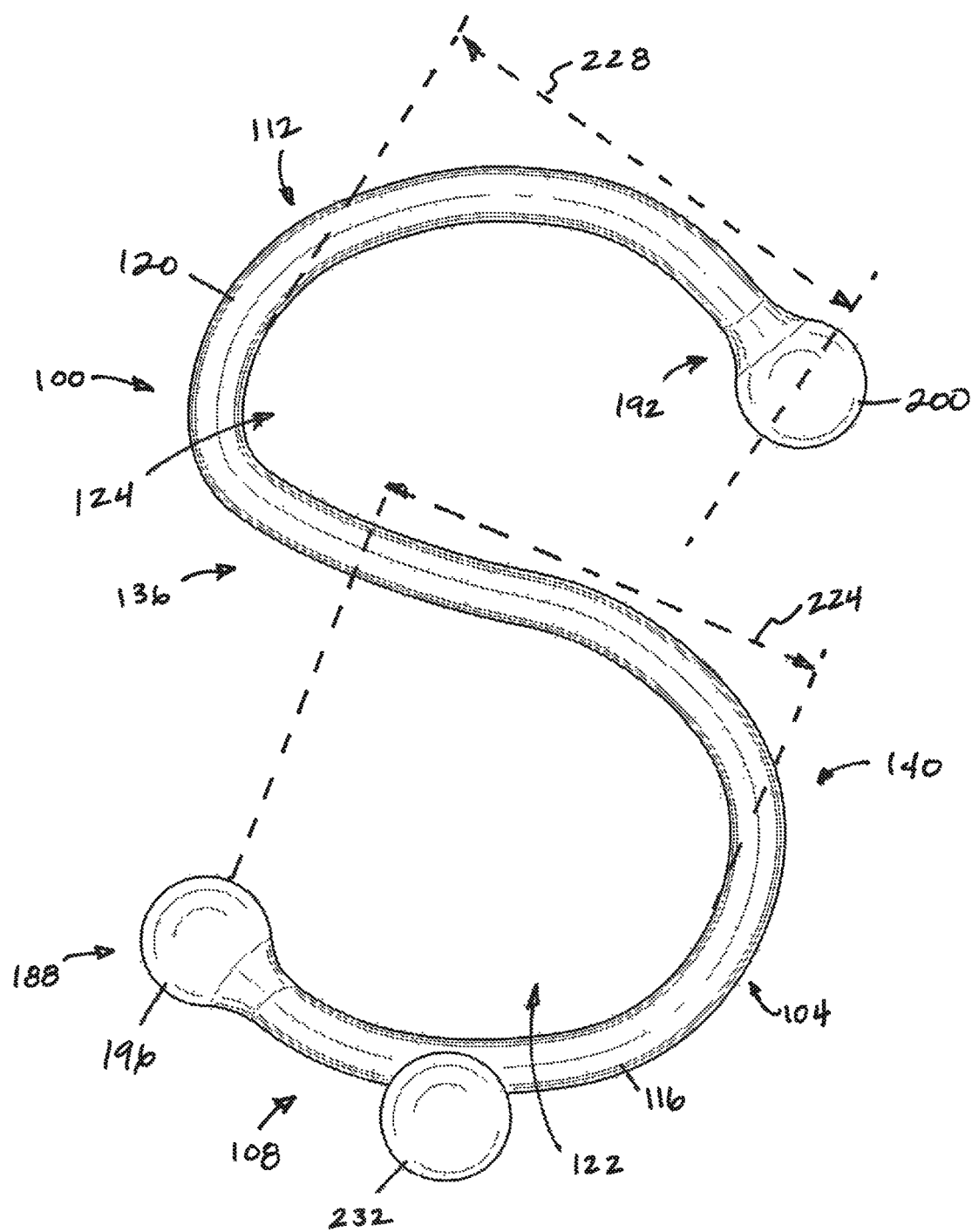
FIG. 4 depicts a bottom view of the apparatus of FIG. 1.

Referring to FIG. 4, first opening 122 of hook 116 and second opening 124 of hook 120 can each have any suitable depth, and such depths can be, but need not be, the same. For example, first opening 122 can have a first maximum depth 224 that is greater than or substantially equal to any one of, or between any two of: 80, 90, 100, 110, 120, 130, 140, 150, 160, or 170% of first minimum width 180 (e.g., between 100 and 150% or between 120 and 135% of the first minimum width). For further example, second opening 124 can have a second maximum depth 228 that is greater than or substantially equal to any one of, or between any two of: 130, 140, 150, 160, 170, 180, 190, 200, 210, or 220% of second minimum width 184 (e.g., between 150 and 200% or between 175 and 185% of the second minimum width). A maximum depth (e.g., 224) of an opening (e.g., 122) can be a maximum distance, measured perpendicularly to a minimum width (e.g., 180) of the opening, between a line that is aligned with the minimum width of the opening and a portion of its respective body (e.g., 104); the maximum depth can be measured when the body is in an unflexed state.

Apparatus 100 includes an arm 232 coupled to and extending downward from a portion of body 104 that defines first hook 116. When a member of a device is disposed within opening 122 of hook 116, arm 232 can restrict movement of apparatus 100 relative to the device (e.g., via physical interaction with the device), facilitate retention of the member within the opening (e.g., at least a portion of the member can be captured between the arm and the hook, as shown for arm 268 of bed 256 in FIG. 11 and for slot or bar 276 of crib 272 in FIG. 12), and/or the like. Embodiments of the present apparatuses can include any suitable number of arms (e.g., (e.g., 232) (e.g., 1, 2, 3, 4, or more arm(s)); each of such arm(s) can be coupled to a portion of a body (e.g., 104) that defines a first hook (e.g., 116) or a portion of the body that defines a second hook (e.g., 120), and the arm can extend downwardly or upwardly from that portion.

Arm 232 is defined by an elongated member 236, which, in this embodiment, has a circular cross-section that is substantially constant along a majority of its length (measured along the elongated member). In other embodiments, an arm can be defined by an elongated member having any suitable cross-section, such as, for example, one that is triangular, rectangular, otherwise polygonal, circular, elliptical, or otherwise rounded, and the cross-section of the elongated member can be substantially constant or varying (e.g., in shape and/or dimensions) along any portion of its length.

Figure 5:
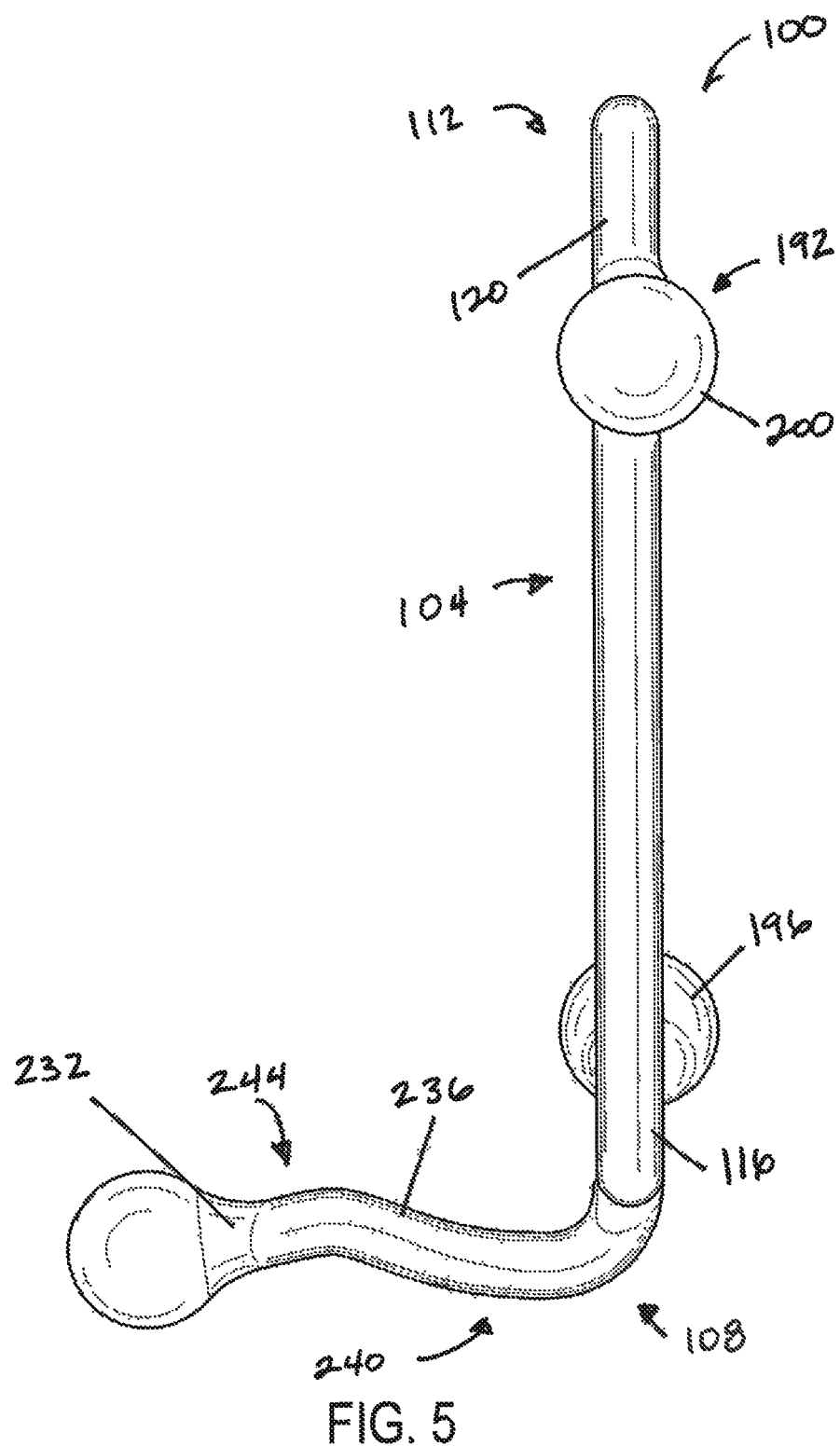
FIG. 5 depicts a back view of the apparatus of FIG. 1.
Figure 6:
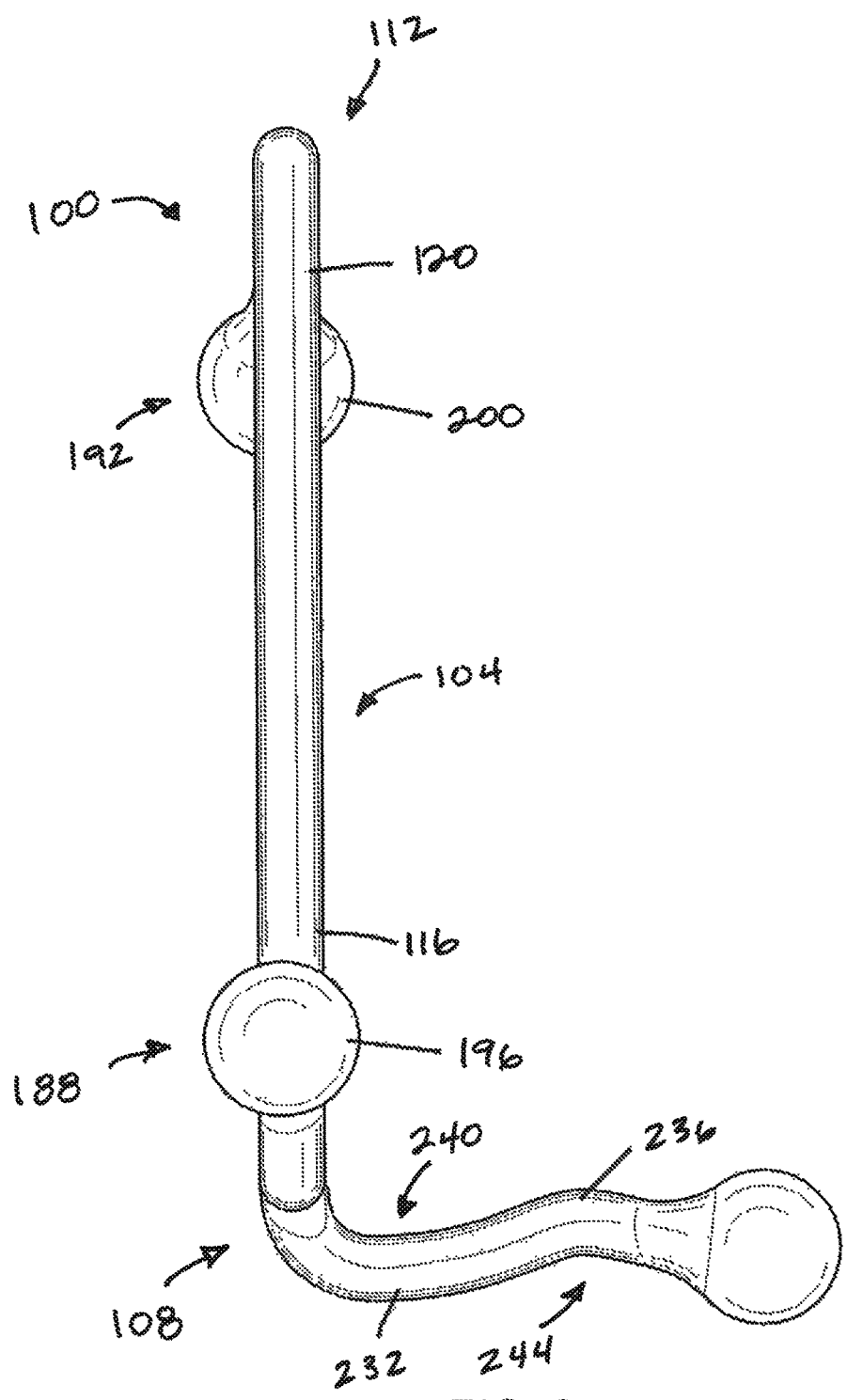
FIG. 6 depicts a front view of the apparatus of FIG. 1.
Figure 7:
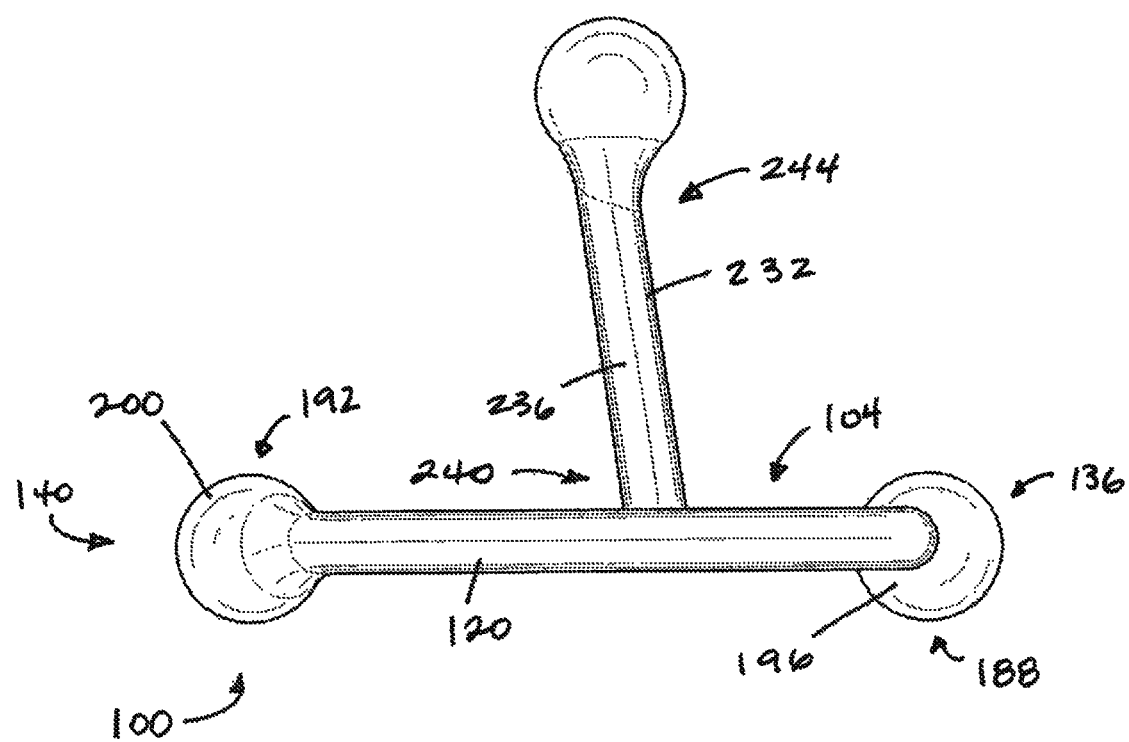
FIG. 7 depicts a left side view of the apparatus of FIG. 1.
Figure 8:
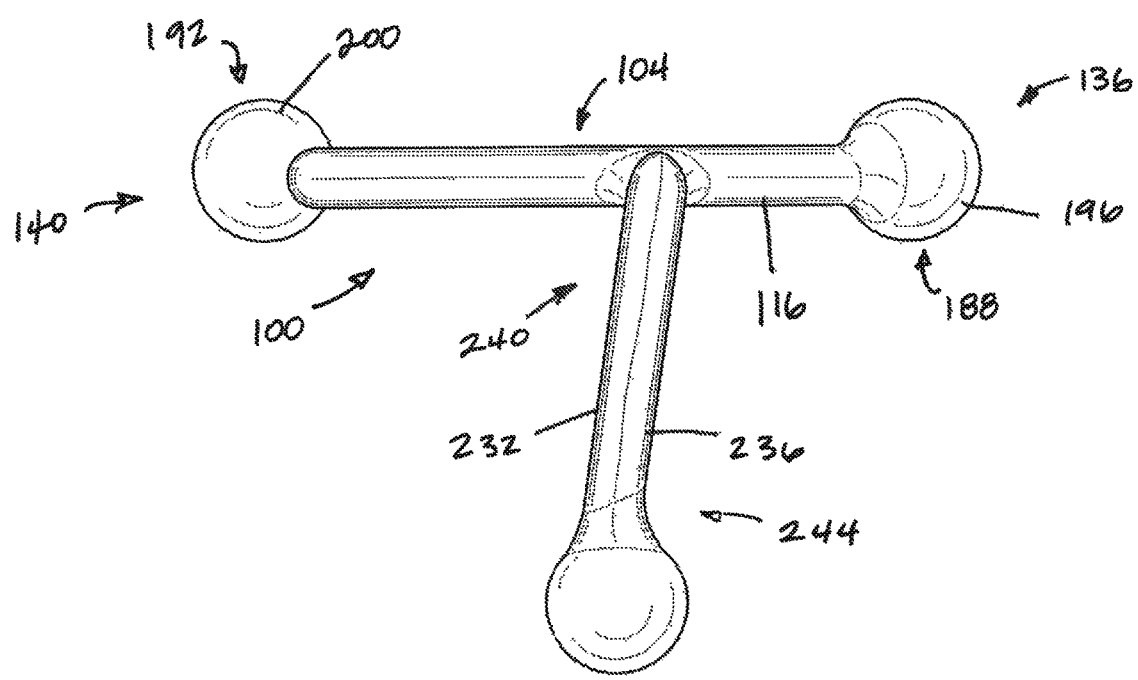
FIG. 8 depicts a right side view of the apparatus of FIG. 1.

In the depicted embodiment, arm 232 is not perpendicular to plane 160 of first hook 116. For example, arm 232 includes an upper portion 240 that extends outward from first side 108 of body 104 and bends back inward toward second side 112 of the body (FIGS. 5 and 6). For further example, arm 232 includes a lower portion 244 that extends inward toward second side 112 of body 104 and bends back outward away from the second side of the body. Arm 232 includes an enlarged portion (e.g., a sphere) at its end that has a larger cross-section than other portions of the arm. Such features can enhance an ability of arm 232 to restrict movement of apparatus 100 relative to a device and/or facilitate retention of a member of the device within opening 122.

Arm 232 can comprise any suitable length. For example, the length of arm 232 can be greater than or substantially equal to any one of, or between any two of: 80, 85, 90, 95, 100, 105, 110, 115, 120, 125, 130, 135, 140, or 145% of first minimum width 180 (e.g., between 100 and 125% of the first minimum width).

Figure 9:
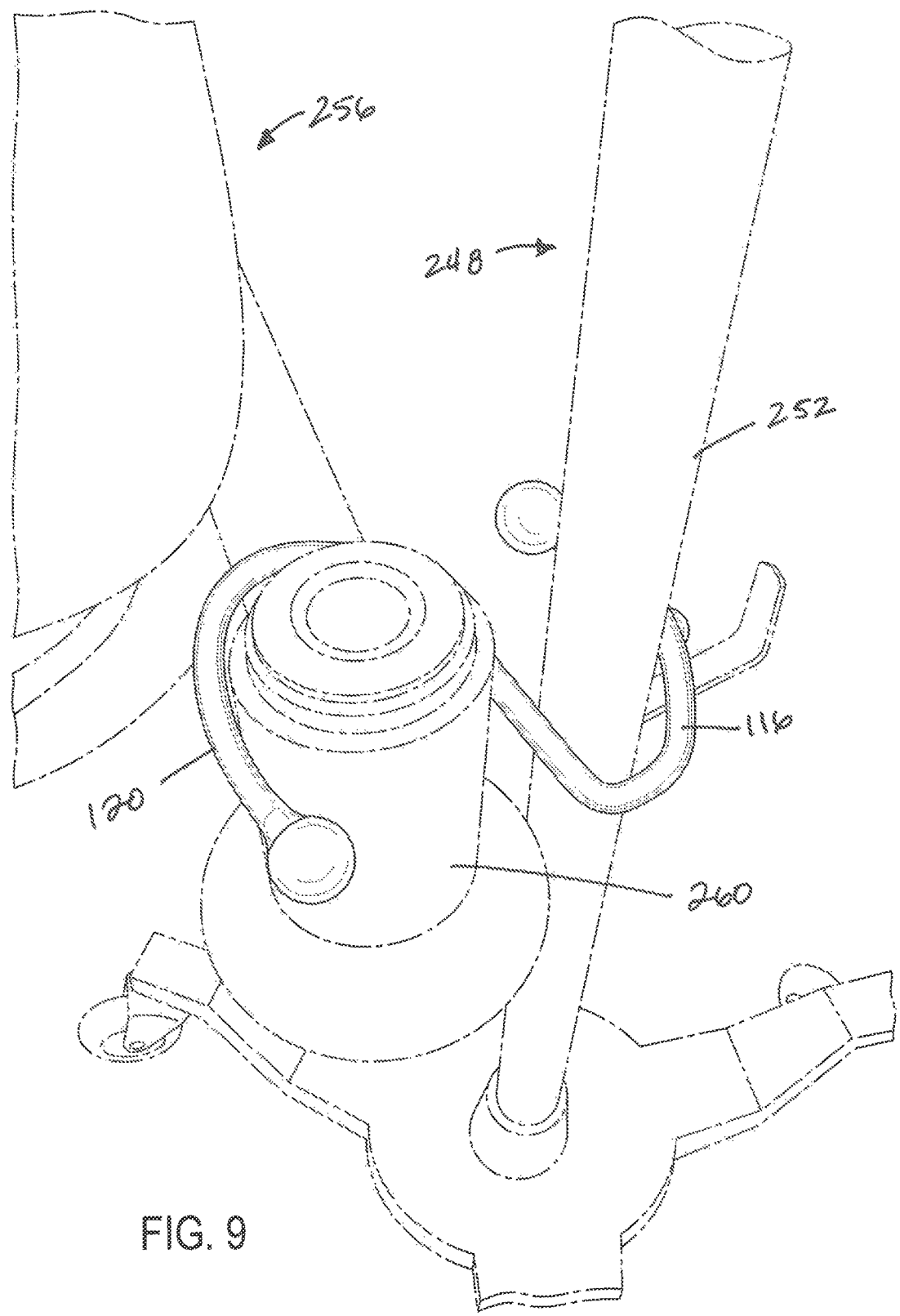
FIG. 9 depicts a perspective view of the apparatus of FIG. 1, shown securing a rollable IV pole relative to a first part of a hospital bed.
Figure 10:
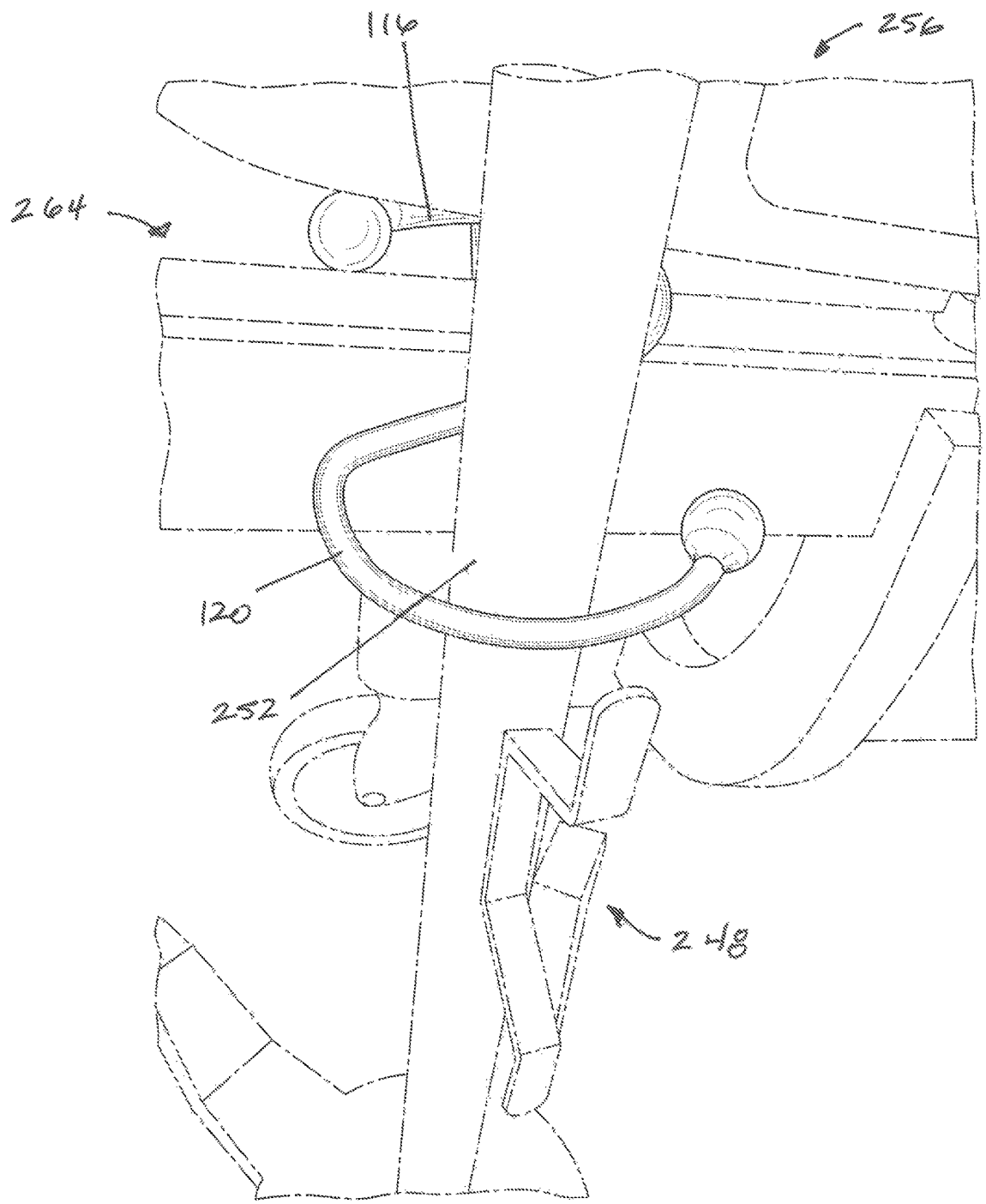
FIG. 10 depicts a perspective view of the apparatus of FIG. 1, shown securing a rollable IV pole relative to second part a hospital bed.
Figure 11:
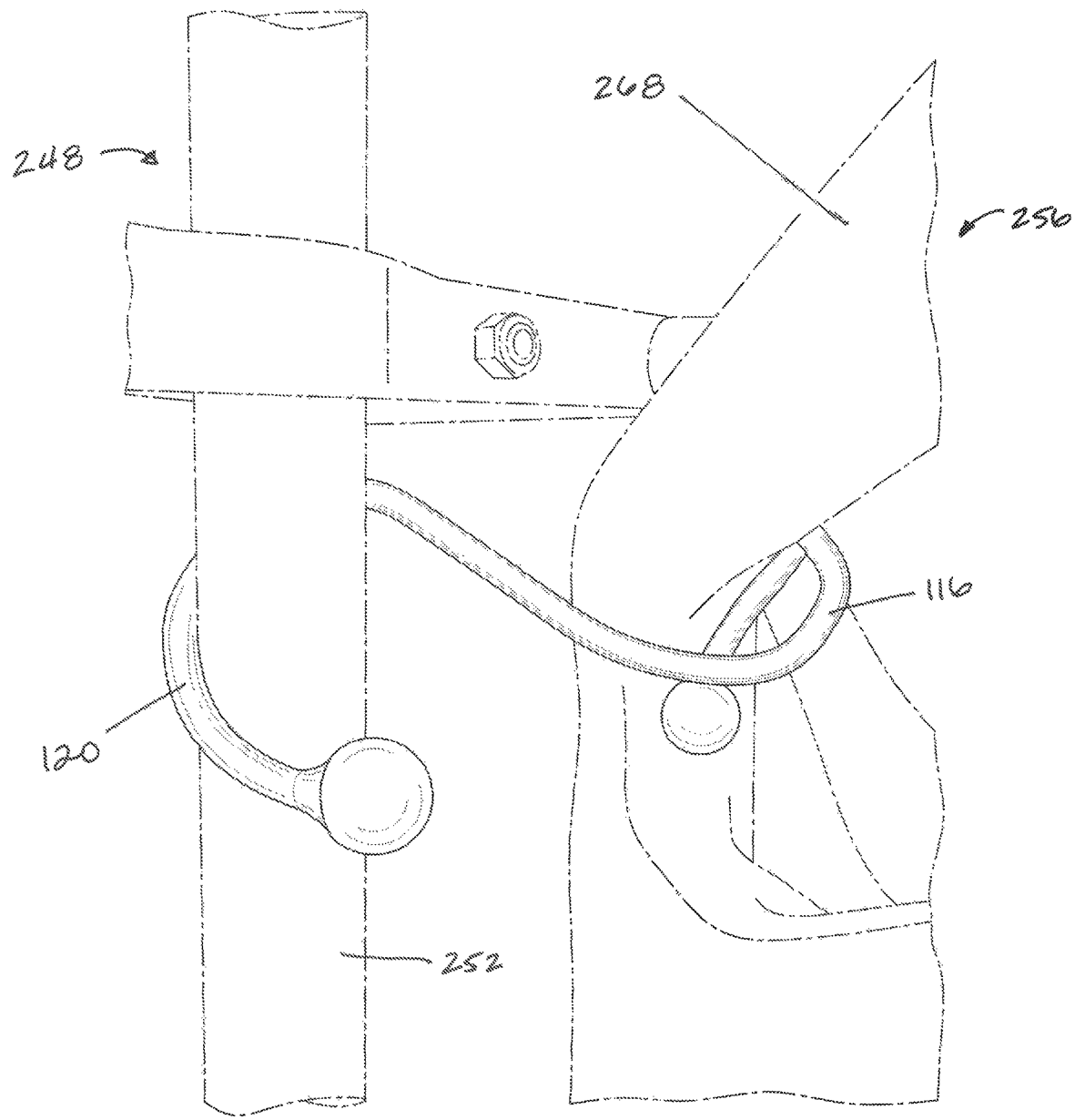
FIG. 11 depicts a perspective view of the apparatus of FIG. 1, shown securing a rollable IV pole relative to a third part of a hospital bed.
Figure 12:
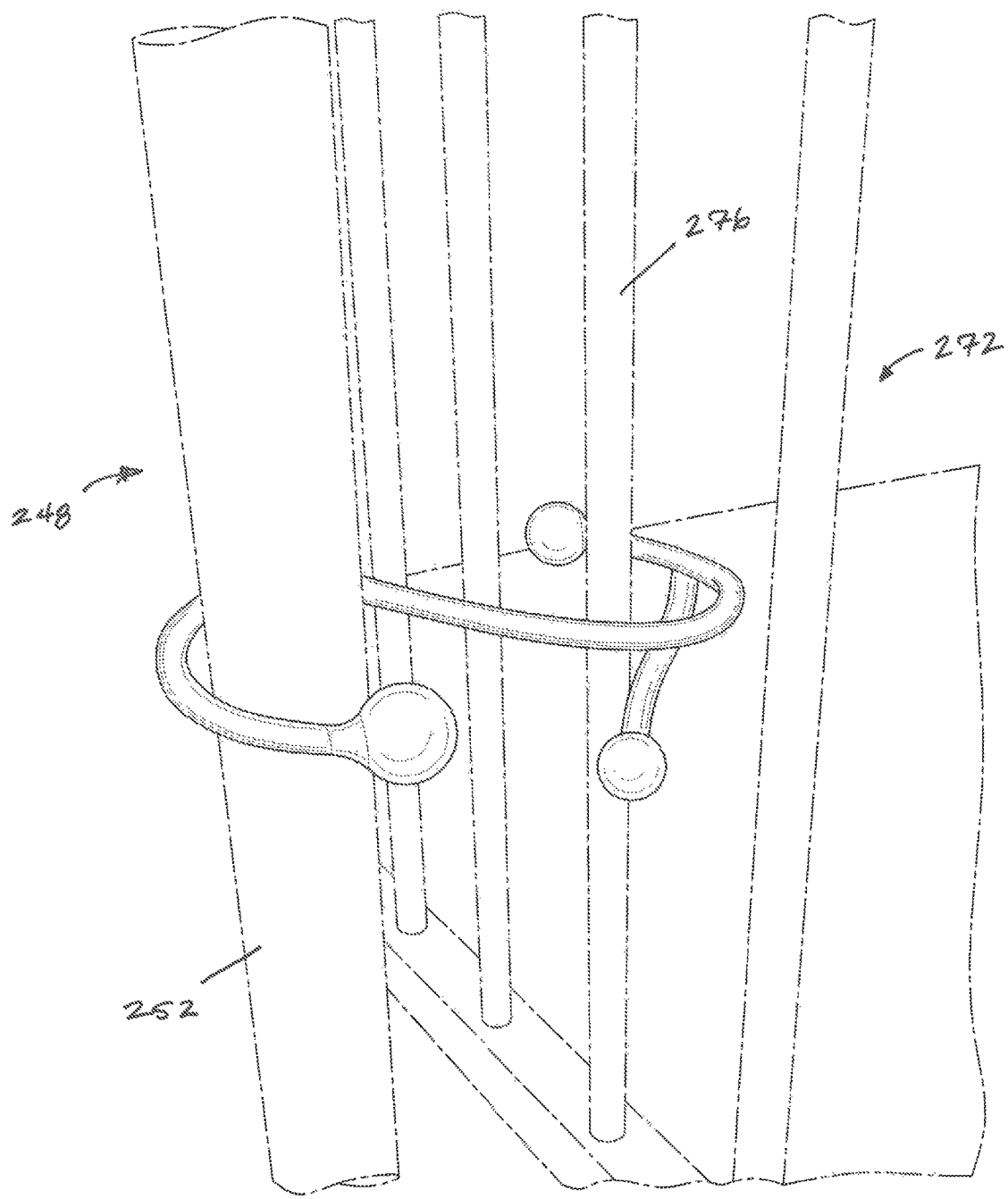
FIG. 12 depicts a perspective view of the apparatus of FIG. 1, shown securing a rollable IV pole relative to a crib.
Figure 13:
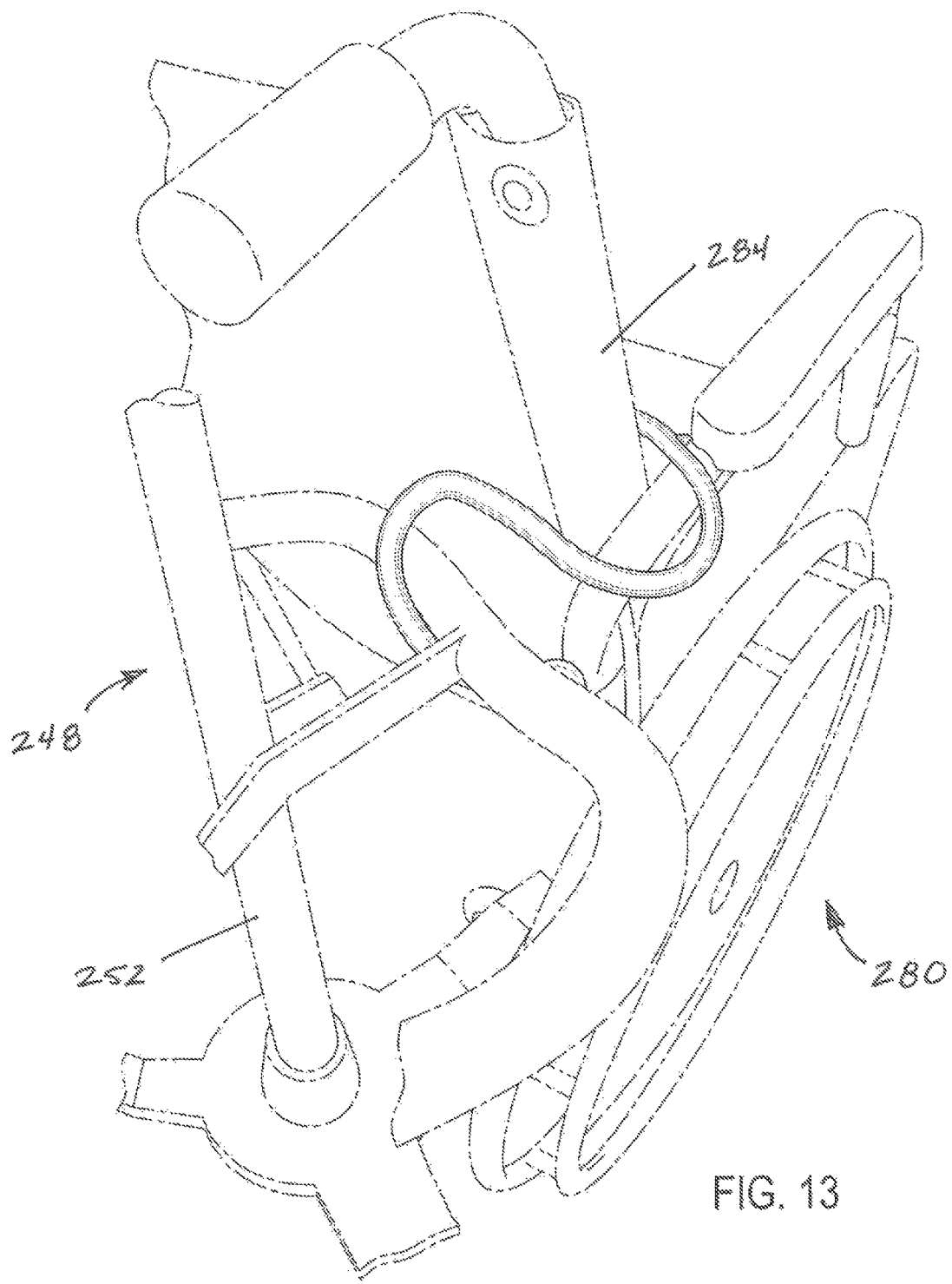
FIG. 13 depicts a perspective view of the apparatus of FIG. 1, shown securing a rollable IV pole relative to a wheelchair.

FIGS. 9-13 depict exemplary uses for the present apparatuses. For example: (1) FIG. 9 depicts apparatus 100 with first hook 116 coupled to a post 252 of an IV rack 248 and second hook 120 coupled to a leg 260 of a bed 256; (2) FIG. 10 depicts apparatus 100 with first hook 116 coupled to a frame 264 of a bed 256 and second hook 120 coupled to a post 252 of an IV rack 248; (3) FIG. 11 depicts apparatus 100 with first hook 116 coupled to an arm 268 of a bed 256 and second hook 120 coupled to a post 252 of an IV rack 248; (4) FIG. 12 depicts apparatus 100 with first hook 116 coupled to a slot or bar 276 of a crib 272 and second hook 120 coupled to a post 252 of an IV rack 248; and (5) FIG. 13 depicts apparatus 100 with first hook 116 coupled to a back 284 of a wheel chair 280 and second hook 120 coupled to an IV rack 248. In each instance, due to apparatus 100, movement of the movable patient-transfer device (e.g., bed 256, crib 272, or wheel chair 280) can cause movement of the movable accessory device (e.g., IV rack 248).

Some embodiments of the present methods for temporarily securing a movable accessory structure relative to a movable patient-support structure comprise: disposing a first member of the patient-support structure within a first hook (e.g., 116) of one of the present apparatuses (e.g., 100), disposing a second member of the accessory support structure within a second hook (e.g., 120) of the apparatus, and moving the accessory support structure by moving the patient-support structure. In some methods, the patient-support structure comprises a bed (e.g., 256), a crib (e.g., 272), an isolette, a radiant warmer, or a wheel chair (e.g., 280). In some methods, the accessory structure comprises an IV pole (e.g., 248), a sensor platform, an ultrasound cart, a crash cart, or a patient ventilator.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus for temporarily securing a movable accessory structure relative to a movable patient-support structure, the apparatus comprising:
an S-shaped body having a front, a back, a top, a bottom, a first side, a second side, and a longitudinal axis extending through the first and second sides, the body defining a first hook on the first side, a second hook on the second side, and a medial portion extending between the first hook and the second hook, the first hook opening toward the front of the body to define a first opening, and the second hook opening toward the back of the body to define a second opening;

wherein the first opening has a first mouth at the front of the body, the first mouth being defined by a first minimum width between a free end of the first hook and the medial portion;

wherein the second opening has a second mouth at the back of the body, the second mouth being defined by a second minimum width between a free end of the second hook and the medial portion;

wherein the first opening and the second opening are aligned and opposite one another, the first opening and the second opening being separated by the medial portion, and wherein the longitudinal axis extends through the first opening, the second opening, and the medial portion, such that an entirety of the first mouth lies on one side of the longitudinal axis and an entirety of the second mouth lies on an opposite side of the longitudinal axis; and wherein the first hook is dimensioned to receive a first member of the patient-support structure, and the second hook is dimensioned to receive a second member of the accessory structure, such that the body will resist separation of the accessory structure from the patient-support structure during movement of the patient-support structure.

2. The apparatus of claim 1, where the body is defined by an elongated member having a substantially constant cross-section along a majority of its length.

3. The apparatus of claim 1, comprising an arm coupled to and extending downward from a portion of the body defining the first hook.

4. The apparatus of claim 3, where the arm is defined by an elongated member having a substantially constant cross-section along a majority of its length.

5. The apparatus of claim 3, where the arm is not perpendicular to a plane of the first hook.

6. The apparatus of claim 3, where the arm has a length that is between 100% and 125% of the first minimum width of the first opening.

7. The apparatus of claim 3, where an upper portion of the arm extends outward from the first side of the body and bends back inward toward the second side of the body.

8. The apparatus of claim 7, where a lower portion of the arm extends inward toward the second side of the body and bends back outward away from the second side of the body.

9. The apparatus of claim 1, where the first hook terminates in a first end with a cross-section that is enlarged relative to that of a majority of the first hook.

10. The apparatus of claim 9, where the second hook terminates in a second end with a cross-section that is enlarged relative to that of a majority of the second hook.

11. The apparatus of claim 1, where the body is configured to permit the first hook to flex to receive a first member having a first transverse dimension that is larger than the first minimum width, and to permit the second hook to flex to receive a second member having a second transverse dimension that is larger than the second minimum width.

12. The apparatus of claim 1, where the second minimum width is between 100% and 150% of the first minimum width.

13. The apparatus of claim 12, where the second minimum width is between 120% and 135% of the first minimum width.

14. The apparatus of claim 12, where the first opening has a first maximum width that is larger than the first minimum width, and the first hook has a first maximum depth that is between 100% and 150% of the first minimum width.

15. The apparatus of claim 14, where the first maximum depth is between 120% and 135% of the first minimum width.

16. The apparatus of claim 12, where the second opening has a second maximum width that is larger than the second minimum width, and the second hook has a second maximum depth that is between 150% and 200% of the second minimum width.

17. The apparatus of claim 16, where the second maximum depth is between 175% and 185% of the second minimum width.

18. The apparatus of claim 1, where the first hook lies in a first plane, and the second hook lies in a second plane that is angled along the longitudinal axis by 0 degrees to 30 degrees relative to the first plane.

19. The apparatus of claim 1, where the patient-support structure is a bed, a crib, an isolette, a radiant warmer, or a wheel chair.

20. A method for temporarily securing a movable accessory structure relative to a movable patient-support structure, the method comprising:

disposing a first member of the patient-support structure within the first hook of the apparatus of any of claims 1-19;

disposing a second member of the accessory structure within the second hook of the apparatus; and moving the accessory structure by moving the patient-support structure.

21. The method of claim 20, where the patient-support structure is a bed, a crib, an isolette, a radiant warmer, or a wheel chair.

22. The method of claim 20, where the accessory structure comprises an IV pole, a sensor platform, an ultrasound cart, a crash cart, or a patient ventilator.

* * * * *